(12) United States Patent
Smith et al.

(10) Patent No.: US 7,704,558 B2
(45) Date of Patent: Apr. 27, 2010

(54) CLEANING ARTICLE CONTAINING HYDROPHILIC POLYMERS

(75) Inventors: James A. Smith, Chatham, MA (US); George Kellett, Cranford, NJ (US)

(73) Assignee: Regenesis, LLC, Montclair, NJ (US)

(*) Notice: Subject to any disclaimer, the term of this patent is extended or adjusted under 35 U.S.C. 154(b) by 0 days.

(21) Appl. No.: 12/006,854

(22) Filed: Jan. 7, 2008

(65) Prior Publication Data

US 2008/0299319 A1    Dec. 4, 2008

Related U.S. Application Data

(62) Division of application No. 11/008,679, filed on Dec. 9, 2004, now Pat. No. 7,332,224, which is a division of application No. 10/293,812, filed on Nov. 13, 2002, now Pat. No. 6,846,480.

(60) Provisional application No. 60/337,512, filed on Dec. 7, 2001.

(51) Int. Cl.
B05D 3/02    (2006.01)

(52) U.S. Cl. .............. 427/385.5; 427/389.9; 427/391; 427/392; 427/394; 427/395; 427/396

(58) Field of Classification Search .............. None
See application file for complete search history.

(56) References Cited

U.S. PATENT DOCUMENTS

| | | | |
|---|---|---|---|
| 3,778,332 A | 12/1973 | Butler et al. | 428/220 |
| 3,833,386 A | 9/1974 | Wood et al. | 106/41 |
| 3,890,254 A | 6/1975 | Guthrie | 260/2.5 BD |
| 3,975,350 A | 8/1976 | Hudgin et al. | 260/30.4 N |
| 4,066,394 A | 1/1978 | Leonard | 8/137 |
| 4,066,578 A | 1/1978 | Murch et al. | 260/2.5 AG |
| 4,137,200 A | 1/1979 | Wood et al. | 521/159 |
| 4,160,076 A | 7/1979 | Guthrie et al. | 521/159 |
| 4,271,272 A | 6/1981 | Strickman et al. | 521/110 |
| 4,309,509 A | 1/1982 | Wood | 521/132 |
| 4,421,526 A | 12/1983 | Strickman et al. | 51/296 |
| 4,503,475 A * | 3/1985 | Hall | 360/137 |
| 4,594,362 A | 6/1986 | Smith et al. | 521/52 |
| 4,654,234 A * | 3/1987 | Rosin et al. | 427/393.5 |
| 4,743,673 A | 5/1988 | Johnston et al. | 528/60 |
| 4,767,825 A | 8/1988 | Pazos et al. | 525/408 |
| 4,769,013 A * | 9/1988 | Lorenz et al. | 604/265 |
| 4,789,720 A | 12/1988 | Teffenhart | 528/76 |
| 4,798,876 A | 1/1989 | Gould et al. | 525/457 |
| 4,806,598 A | 2/1989 | Morman | 525/63 |
| 4,810,543 A | 3/1989 | Gould et al. | 428/35.7 |
| 4,810,582 A | 3/1989 | Gould et al. | 428/423.1 |
| 4,820,577 A | 4/1989 | Morman et al. | 428/228 |
| 4,828,911 A | 5/1989 | Morman | 428/288 |

(Continued)

FOREIGN PATENT DOCUMENTS

WO    WO 02/092052 A2    11/2002

*Primary Examiner*—Erma Cameron
(74) *Attorney, Agent, or Firm*—Nash and Titus, LLC

(57) ABSTRACT

The invention relates to a cloth that can function as a moisturizing cleanser. When the cloth is moistened with water, it works up into a warm, sudsy cleansing lotion that feels great and works well as a facial cleansing cloth. The cloth contains water, at least one surfactant and at least one hydrophilic polymer.

9 Claims, 1 Drawing Sheet

U.S. PATENT DOCUMENTS

| | | |
|---|---|---|
| 4,847,141 A | 7/1989 | Pazos et al. ............. 428/226 |
| 4,920,172 A | 4/1990 | Daoud ................... 524/502 |
| 4,948,585 A | 8/1990 | Schlein ................. 424/404 |
| 4,963,638 A | 10/1990 | Pazos et al. ............. 528/65 |
| 5,000,948 A | 3/1991 | Nandagiri et al. ......... 424/71 |
| 5,120,816 A | 6/1992 | Gould et al. ............. 528/76 |
| 5,334,691 A | 8/1994 | Gould et al. ............. 528/76 |
| 5,538,732 A | 7/1996 | Smith et al. ............. 424/402 |
| 5,563,233 A | 10/1996 | Reich et al. ............. 528/76 |
| 5,620,694 A | 4/1997 | Girardot ................. 424/402 |
| 5,650,225 A | 7/1997 | Dutta et al. ............. 428/318.4 |
| 5,728,762 A | 3/1998 | Reich et al. ............. 524/379 |
| 5,744,149 A | 4/1998 | Girardot ................. 424/402 |
| 5,932,200 A | 8/1999 | Reich et al. ............. 424/65 |
| 5,962,620 A | 10/1999 | Reich et al. ............. 528/76 |
| 5,972,361 A | 10/1999 | Fowler et al. ............ 424/402 |
| 5,980,931 A | 11/1999 | Fowler et al. ............ 424/443 |
| 6,001,380 A | 12/1999 | Smith et al. ............. 424/402 |
| 6,060,149 A | 5/2000 | Nissing et al. ........... 428/138 |
| 6,063,397 A | 5/2000 | Fowler et al. ............ 424/443 |
| 6,074,655 A | 6/2000 | Fowler et al. ............ 424/402 |
| 6,096,726 A | 8/2000 | Opolski .................. 514/53 |
| 6,117,489 A | 9/2000 | Ohkawa et al. ............ 427/331 |
| 6,132,746 A | 10/2000 | Hasenoehrl et al. ........ 424/402 |
| 6,133,212 A | 10/2000 | Elliott et al. ........... 510/159 |
| 6,153,208 A | 11/2000 | McAtee et al. ............ 424/402 |
| 6,190,678 B1 | 2/2001 | Hasenoehrl et al. ........ 424/401 |
| 6,191,083 B1 | 2/2001 | Brooks et al. ............ 510/124 |
| 6,267,975 B1 | 7/2001 | Smith et al. ............. 424/401 |
| 6,277,386 B1 | 8/2001 | Kim et al. ............... 424/401 |
| 6,280,757 B1 | 8/2001 | McAtee et al. ............ 424/402 |
| 6,303,119 B1 | 10/2001 | Weisgerber et al. ........ 424/94.63 |
| 6,338,855 B1 | 1/2002 | Albacarys et al. ......... 424/409 |
| 6,488,570 B1 | 12/2002 | James et al. ............. 451/36 |
| 6,706,775 B2 | 3/2004 | Hermann et al. ........... 521/134 |
| 2001/0000785 A1 | 5/2001 | Opolski .................. 514/53 |

* cited by examiner

CLEANING ARTICLE CONTAINING HYDROPHILIC POLYMERS

RELATED APPLICATIONS

This application is a divisional application of Ser. No. 11/008,679, filed Dec. 4, 2004, now U.S. Pat. No. 7,332,224 B2, which is a divisional application of Ser. No. 10/293,812, filed Nov. 13, 2002, now U.S. Pat. No. 6,846,480 B2, issued Jan. 25, 2005, which claims benefit to provisional application Ser. No. 60/337,512 filed Dec. 7, 2001 which is incorporated by reference in its entirety for all useful purposes.

FIELD OF THE INVENTION

The invention relates to a cloth that can function as a moisturizing cleanser. When the cloth is moistened with water, it works up into a warm, sudsy cleansing lotion that feels great and works well as a facial cleansing cloth.

BACKGROUND OF THE INVENTION

The problems encountered in producing foam-based sheets or pads designed to meet household cleaning needs have been addressed by a variety of products. Polyurethane foam-based sponge products which have been disclosed fall into two general classes, which may be designated as dry and moist. Dry sponge products are disclosed by Strickman et al in U.S. Pat. Nos. 4,271,272 and 4,421,526. These products are formed by reacting isocyanate-capped polypropylene glycol resins with small amounts of water and organic catalysts, followed by stirring powdered detergents and/or abrasives into the foaming resin. Since the molar ratio of water to free isocyanate groups on the resin is generally adjusted to about 0.5 or less, the cured foam which is obtained is dry. This results in additives such as abrasives and detergents being largely deposited in the cell voids, thus reducing the sponge's absorbency. When the sponges are remoistened, the additives must re-emulsify prior to becoming available for application in a cleaning operation.

Other dry water activated delivery system are described in U.S. Pat. Nos. 6,001,380 and 5,538,732.

The preparation of open-called, hydrophilic or "moist" polyurethane foams by the reaction of specially-formulated prepolymer isocyanate resins with large molar excesses of water without the need for added catalysts or cross-linking agents is disclosed in U.S. Pat. Nos. 3,890,254; 4,137,200 and 4,160,076. These resins permit the introduction of large amounts of solids into the form matrices via preformed aqueous slurries of solid particles which are subsequently reacted with the prepolymer resin in order to foam it into the desired specialty product. The finished foams are very hydrophilic, or water-absorbent, due to the entrapment of excess water within the cell walls.

U.S. Pat. Nos. 3,833,386; 4,066,394; 4,066,578; 4,309,509; and 3,343,910 describe the incorporation into hydrophilic forms of sinterable ceramic materials, water-softening minerals such as zeolites, flame retardants, ordorant-containing waxes and fine abrasives, respectively. In order to produce solids-loaded foams for use as polishing pads, sachets, water-softening sponges, cushions and the like, the weight ratio of aqueous phase to resin must be maintained at a value low enough so that the foam matrix exhibits satisfactory overall integrity. Increasing the weight of additives in foamed products formed by this method necessarily requires the use of higher ratios of water to prepolymer resin, which in turn attenuates the polymeric cellular matrix which is further embrittled by the introduction of the solids. Surfactants which result in a highly reticulated, open-celled matrix also reduce the absolute strength of the foam due to the removal of cell window membranes. Although reticulated, open-celled, hydrophilic polyurethane foams which are highly loaded with particulate abrasives are desirable due to their optimal cleaning power, when the weight ratio of dispersed abrasives in the aqueous phase to the presently-available prepolymer resins exceeds a certain value, the resultant foams will become friable. These foams are unsuitable for use as cleaning pads and sheets due to their low tensile strength which causes the cured foams to flake or crumble during use.

U.S. Pat. No. 4,581,287 describes the use of foam-textile cleaning pads.

U.S. Pat. No. 5,53,732 ("'732 patent") discloses a medicated applicator sheet for topical delivery for skin diseases, such as acne. A flexible base sheet is impregnated with impregnated with first and second solid or semi-solid compositions comprising first and second dermatological agents, each confined to first and second discrete areas, respectively. The compositions are preferably anhydrous. However, the examples show the water can be added. The '732 patent does not teach using a hydrophilic polymer.

The following United States patents are assigned to The Procter & Gamble Company and are directed to personal care compositions: U.S. Pat. Nos. 6,303,119; 6,280,757; 6,267,975; 6,190,678 and 6,153,208 which are all incorporated by reference in their entirety for all useful purposes.

SUMMARY OF THE INVENTION

Thus, it is an object of the present invention to provide cleaning pads or sheets comprising a hydrophilic polymer, water and at least one surfactant.

It is another object of the present invention to provide resilient cleaning pads or sheets suitable for cleaning a wide variety of surfaces.

Another aspect of the invention is as follows: formulating a good quality aqueous facial cleansing system, (1) adding at least one surfactant, (2) water and then combining this aqueous phase with (2) a hydrophilic polymer such as a polyurethane prepolymer. Other hydrophilic polymers or combination of polymers can be used. Optionally, other ingredients, such as organic or inorganic fillers, abrasives, moisturizers, detergents, fragrances, etc. can be added to the aqueous phase. The resultant reaction mixture is coated on a material, such as a paper, fabric or flexible foam. The final sheet becomes a flexible polymeric film, dried, cut into desired sizes and packaged.

Depending on the amount of polymer in the system, there can be a moist ready to use skin care product (that could be considered remoistened) or one, as in the case described above, that contains low levels of water that is subsequently dried off as described above. The resultant coated sheet is easily activated by wetting with water forming a rich, sudsy cleansing system on a wash cloth.

An important aspect of the invention is the use of a film forming polymer and in particular, a hydrophilic polyurethane polymer. It allows the following: (1) the ability to provide much higher levels of surfactants and moisturizes for coating on substrates, (2) the ability to include (organic or inorganic) fillers that can be attached into the polymer chain by using organosilanes or not. The fillers can be abrasive for a deeper skin cleaning capability or short fibers for increased time release activity of the active ingredients, (3) the ability to absorb water without dissolving itself during the cleaning step, and (4) providing integrity to the sheet or pad, which would enable the use of very light weight nonwoven or paper materials.

Furthermore, it is feasible to use other hydrophilic polymers that would dissolve or solubilize with water when moistened. They could contain the same high levels of surfactants as well.

The objects of the present invention are accomplished by a film made without the use of foam or the requirement to be a foam material. In addition, the cleansing sheet does not require the use of an enzyme, such as Protease G enzyme which is required in U.S. Pat. No. 6,303,119. This enzyme can be excluded from this invention. The film coating does not require and can be made without a foam coupling agent being present. Other objects and advantages of the present invention will become apparent from the following description and appended claims.

DETAILED DESCRIPTION OF THE INVENTION

Figure 1:
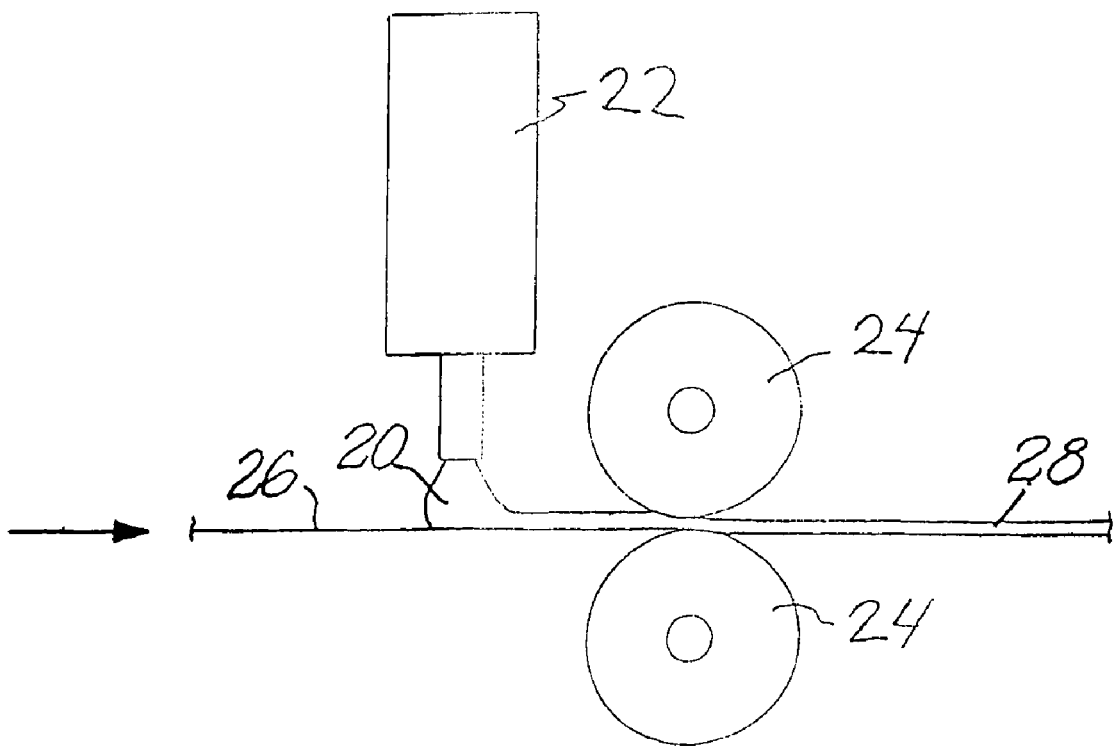
FIG. 1 illustrates a process to make the sheet according to the invention.

The composite cleaning pads or sheets of the present invention are prepared by a process comprising forming an aqueous slurry which includes a hydrophilic polymer, at least one surfactant and water.

FIG. 1 illustrates the preferred technique to make the coated fabric. Water, at least one surfactant and a hydrophilic polymer are mixed together in a mixer 22 to form a wet mixture 20. As the wet mixture 20 comes out of the mix head, it is rolled in between rollers 24 for impregnating into the sheet 26 as a cleansing film or cleaning sheet 28 rather than the traditional hydrophilic foam. The film is dried by any conventional means such as in an oven. After the film is dried, the film is then processed into sheets as disposable wash cloths.

Sheet

The textile sheet is preferably, a nonwoven. The non-woven can also be what is called "apertured"—in other words, there are uniform spaces that go right through the nonwoven and made with water jets (apparently there are several suppliers that produce this type of fabric) using specialized equipment. The skin care coating is on each strand of nonwoven and not in the voids. However, non-apertured nonwovens can also be used.

The textile sheet may be selected from any of the natural or synthetic, woven or nonwoven fabrics which posses sufficient hydrophilicity to remain firmly bonded to the layer during use and which posses sufficient tensile strength to prevent the sheet from cracking or separating during use. A preferred nonwoven fabric comprises a polyester/rayon blend, most preferably a 70-80% polyester, 20-30% rayon blend such as are available from Precision Custom Coatings in weights of about 1.0-5.0 oz./yd. Multi-ply textiles may be employed, thus allowing the preparation of cleaners in which the thickness of the cloth portion is equal to or exceeds that of the sheet.

The hydrophilic polyurethane coating can be easily applied to the traditional nonwoven fabrics as a total overcoat or applied in a variety of patterns. Coatings can be applied to paper, urethane foams, etc. just as well.

Formulations

The composition comprises an aqueous composition which contains water, at least one surfactant and at least one hydrophilic polymer. The composition can optionally be combined with fillers, abrasives, moisturizers, detergents, fragrances, etc.

Hydrophilic polymers in combination with other polymers, such as polysaccharides (chitins, celluloses, modified celluloses, etc.) could be especially useful. The polymer film allows thinner, less strong nonwoven fabrics to be used, because the film adds strength and body.

Hydrophilic Polymer

The hydrophilic polymer is present in an amount from 0.01 to 90%, preferably from 1% to 45%, and most preferably from 25 to 35% based on the total amount of the ingredients present in the slurry. This applies to other hydrophilic polymers—not just the urethane types.

Commercially available class of water prepolymer resins which yield cross-linked, hydrophilic polyurethane upon the addition of stoichiometric excesses of water are those belonging to the Hypol® series (Dow; FHP 3000, 2000, 2000 HD, 2002) which are generally described in U.S. Pat. No. 4,137,200, the disclosure of which is incorporated by reference herein. These liquid resins are prepared by capping mixtures of low molecular weight polyols having 3-8 hydroxyl groups and polyoxyethylene diols with toluene diisocyanate. The capped alcohol mixtures have an average number of free isocyanate groups per molecule which is equal to two or more, i.e., 2-8.

These prepolymer resins can be prepared by polymerizing ethylene oxide to yield polyalkylenoxy polyols having a molecular weight of about 900-1100. These polyols are reacted with a stoichiometric excess of a polyisocyanate. Suitable isocyanates include toluene diisocyanate, triphenylmethane-4,4',4"-triisocyanate, benzene-1,3,5-triisocyanate, hexamethylene diisocyanate, xylene diisocyanate, chlorophenylene diisocyanate and mixtures thereof. The useful resins recovered have a somewhat lower number of mEg of free isocyanate groups (NCO) per gram of resin than do the Hypol® resins, e.g. 1.3-1.5 mEq NCO/gram and exhibit a substantially higher tensile strength when foamed and cured at ambient temperatures to incorporate high percentages of dispersed abrasives.

One such commercially available self cross-linking resin is Trepol® prepolymer resin (Rynel, Boothbay, Me.), which forms acceptable foams upon reaction with at least a stoichiometric excess of water without employing a low molecular weight polyol component to raise the average number of free isocyanate groups per glycol ether molecule to above two. TRE STD®. resin has an average free isocyanate content of about 1.4 mEq./gram, comprises a polyol component having an average molecular weight of about 1000, exhibits a viscosity at 32° C. of 4700 cps and solidifies at 15.5° C.

The preferred hydrophilic polymer is polyurethane polymer used in the preferred system is one made by Rynel, of Boothbay, Me. called Trepol®. It has a rather low NCO content in comparison to other available urethane prepolymers. It is made with lower concentrations of toluene diisocyanate thus providing lower NCO content. The preferred level is 30%, but less can be used—possibly down to 10% and as much as 60% on the high side.

Other polymers are described in the following U.S. Pat. Nos.
6,277,386,
5,962,620,
5,932,200,
5,728,762,
5,650,225,
5,563,233,
5,334,691, 5,120,816,
5,000,948,
4,963,638,
4,920,172,
4,847,141,
4,828,911,
4,820,577,
4,810,582,
4,810,543,
4,806,598,
4,798,876,
4,789,720,
4,767,825,
4,743,673 and
3,975,350.

Other types of "hydrophilic" polymer films such as

Gantrez polymers such as but not limited to polymethyl vinyl ether maleic anhydride, gafquat polymers such as, but not limited to vinyl pyrrolidone/quarternized dimethylaminoethylmethacrylate copolymers, copolymer 845 or 937 which are vinylpyrrolidone/dimethylaminoethylmethacrylate copolymers, PVP/VA series which are vinylpyrrolidone/vinyl acetate copolymers, Ganex polymers which are alkylated vinylpyrrolidone polymers, PVP which is polyvinyl pyrrolidone Polyethylene glycols, Polyacrylate copolymers, PVDC which is polyvinylidene dichloride and combinations thereof.

In addition, combinations of (vinyl acetate, acrylics, etc.), acrylates themselves and blends (polyacrylic acid and others), polyvinyl alcohol, etc. that could be used in place of the urethanes or in combination with the urethanes.

Surfactants

A wide variety of surfactants can be used at levels below 12.5% and even below 10%. Furthermore the surfactants can be at levels as high as about 70%. The surfactants can be nonionic, anionic, cationic zwitterionic and amphoteric, types—alone or in combination. Moreover, soap bases (soap bars) such as sodium stearate and similar bases as found in Dove, Dial, etc. can be used.

The total amount of surfactant, which is preferably used is about 0.05 to about 90%, most preferably in one embodiment in an amount about 1 to about 10% by weight of the aqueous phase. The range is preferably from 8 to 90% and preferably from 20 to 60% by weight.

Preferred nonionic surfactants include the condensation products of ethylene oxide with a hydrophobic polyoxyalkylene base formed by the condensation of propylene oxide with propylene glycol. The hydrophobic portion of these compounds has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product.

Examples of compounds of this type include certain of the commercially-available Pluronic® surfactants (BASF), especially those in which the polyoxypropylene ether has a molecular weight of about 1500-3000 and the polyoxyethylene content is about 35-55% of the molecule by weight, i.e. Pluronic® L-62.

Other useful nonionic surfactants include the condensation products of C8-C22 alkyl alcohols with 2-50 moles of ethylene oxide per mole of alcohol. Examples of compounds of this type include the condensation products of C11-C15 secondary alkyl alcohols with 3-50 moles of ethylene oxide per mole of alcohol which are commercially-available as the Poly-Tergent® SLF series from Olin Chemicals or the Tergitol® series from Union Carbide, i.e. Tergitol® 25-L-7, which is formed by condensing about 7 moles of ethylene oxide with a C12-C15 alkanol.

Other nonionic surfactants which may be employed include the ethylene oxide esters of C6-C12 alkyl phenols such as (nonylphenoxy)polyoxyethylene ether. Particularly useful are the esters prepared by condensing about 8-12 moles of ethylene oxide with nonylphenol, i.e. the Igepal® CO series (GAF Corp., New York, N.Y.).

A further useful class of nonionic surfactant is amine oxides, such as the C10-C20-alkyl-di(lower)alkyl-amine oxides or the C10-C20-alkylamino(C2-5)alkyl di(lower) alkyl-amine oxides. Especially preferred members of this class include lauryl(dimethyl)amine oxide, myristyl(dimethyl)amine oxide, stearyl(dimethyl)amine oxide (Schercamox® DMS, Scher Chemicals, Inc., Clifton, N.J.), coco (bis-hydroxyethyl)amine oxide (Schercamox® CMS), tallow (bis-hydroxyethyl)amine oxide, cocoamidopropyl amine oxide and cocoamidopropyl(dimethyl)amine oxide (Schercamox® C-AA).

Another useful class of nonionic surfactant is the silicone-glycol copolymers. These surfactants are prepared by adding poly(lower)alkylenoxy chains to the free hydroxyl groups of dimethylpolysiloxanols and are available from the Dow Corning Corp as Dow Corning 190 and 193 surfactants (CTFA name: dimethicone copolyol.).

Other useful nonionics include the ethylene oxide esters of alkyl mercaptans such as dodecyl mercaptan polyoxyethylene thioether, the ethylene oxide esters of fatty acids such as the lauric ester of polyethylene glycol and the lauric ester of ethoxypolyethylene glycol, the ethylene oxide ethers of fatty acid amides, the condensation products of ethylene oxide with partial fatty acid esters of sorbitol such as the lauric ester of sorbitan polyethylene glycol ether, and other similar materials, wherein the mole ratio of ethylene oxide to the acid, phenol, amide or alcohol is about 5-50:1.

Anionic surfactants preferred are described in the examples and due to their high detergency include anionic detergent salts having alkyl substituents of 8 to 22 carbon atoms such as the water-soluble higher fatty acid alkali metal soaps, e.g., sodium myristate and sodium palmitate. An especially preferred class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group (e.g., sodium dodecylbenzenesulfonate, magnesium tridecylbenzenesulfonate, lithium or potassium pentapropylenebenzenesulfonate). These compounds are available as the Bio-Soft® series, i.e. Bio-Soft D-40 (Stephan Chemical Co., Northfield, Ill.).

Other useful classes of anionic surfactants include the alkali metal salts of alkyl naphthalene sulfonic acids (methyl naphthalene sodium sulfonate, Petro® AA, Petrochemical Corporation); sulfated higher fatty acid monoglycerides such as the sodium salt of the sulfated monoglyceride of coconut oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium laureth sulfate; sodium $C_{14}$-$C_{16}$-alphaolefin sulfonates such as the Bio-Terge® series (Stephan Chemical Co®.); alkali metal salts of sulfated ethyleneoxy fatty alcohols (the sodium or ammonium sulfates of the condensation products of about 3 moles of ethylene oxide with a C.sub.12 14 C.sub.15 n-alkanol, i.e., the Neodol® ethoxysulfates, Shell Chemical Co.); alkali metal salts of higher fatty esters of low molecular weight alkylol sulfonic acids, e.g., fatty acid esters of the sodium salt of isethionic acid; the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toluene sulfonate and mixtures thereof.

A further useful class of anionic surfactants includes the 8-(4-n-alkyl-2-cyclohexenyl)-octanoic acids wherein the cyclohexenyl ring is substituted with an additional carboxylic acid group. These compounds, or their potassium salts, are commercially-available from Westvaco Corporation as Diacid® 1550 or H-240.

Other surfactants are described in U.S. Pat. Nos. 6,133, 212; and 6,191,083 which are incorporated by reference for all useful purposes in their entireties.

Water

The last of the required ingredients is water. Water is present in an amount from 10% to about 85% and preferably from 20% to about 60% based on the total amount of the ingredients present in the slurry.

Optional Ingredients

Fillers

Fillers, such as inorganic or organic fillers can be used. The fillers allow a controlled release of actives (such as surfactants, moisturizers, etc.) from the hydrophilic polyurethane film, as the film absorbs water when wetted.

Organic fillers useful in the practice of the present invention include carboxymethylcellulose, polyvinylpyrrolidone and polymeric organic waxes. The useful polymeric waxes include ethylene acrylate copolymers, ethylene acrylic acid copolymers, and polyethylene (e.g. oxidized polyethylenes). These materials are commercially available in the form of aqueous emulsions or dispersions, e.g. from Allied-Signal, Morristown, N.J., as the A-C Copolymer and A-C Polyethylene series, such as A-C Copolymer 540, A-C Copolymer 580 and A-C Polyethylene 617 and 629.

Preferably, the inorganic fillers employed will comprise those of natural or synthetic of mineral origin. One preferred inorganic filler is diatomaceous earth. Other fillers are the smectite clays such as the saponites colerainites, and sapphires and the montmorillonite colloidal clays (magnesium aluminum silicate) such as Veegum® (Vanderbilt Minerals, Murray, Ky.) or Magnabrite® (American, Colloid Co., Skokie, Ill.). Modified magnesium aluminium silicate materials such as magnesium aluminium silicate mineral/CMC are available from the R.T Vanderbilt Company, Inc. under the trade name Veegum Plus®. This modified clay material contains smectite clay with sodium carboxymethylcellulose and titanium dioxide. Bentonite is a native hydrated colloidal aluminium silicate clay available from ECC America under the trade name Bentonite H (RATM) and from Whittaker, Clark and Daniels under the trade name Mineral Colloid BP 2430®. Hectorite is one of the montmorillonite minerals that is a principal constituent of bentonite clay. Hectorite is available from Rheox Inc. under the trade names Bentone EW® and Macaloid®.

Synthetic sodium magnesium silicate clays and fumed silicas can also be used as fillers.

In addition, silicates can also be used, alone or in combination with the clays to produce fine open-celled foams. Preferred inorganic silicates are the naturally-occurring calcium metasilicates such as wollastonite, available as the NYAD® wollastonite series (Processed Minerals Inc., Willsboro, N.Y.), of which NYAD® 400 is especially preferred.

The filler is preferably is used in amounts from about 1.0% to about 60%, and more preferably from about 4.0% to about 25% based on the total amount of the ingredients present in the slurry.

Abrasives

There can optionally be an abrasive material. The choice of abrasive material may be made from a wide variety of materials of adequate hardness and of a particle size range which will enable them to effectively scour soiled surfaces.

Preferably, the weight of the abrasive used will be from about 0.25% of the prepolymer weight, most preferably 10%.

A preferred abrasive for use in the present invention is (Aluminium Oxide) available from Degussa Corporation, Parsippany, N.J. Among the substances that meet this requirement are minerals such as the feldspars, quartz, aluminas, diatomaceous earths, sands, glasses, naturally-occurring and synthetic zeolites, zircon, carborundum, pumice and the like, which may be used singly or in mixtures.

Moisturizers

Moisturizers can be added to the formula. In preferred embodiments, the moisturizer is selected from:

1. water-soluble liquid polyols;
2. essential amino acid compounds found naturally occurring in the stratum corneum of the skin; and
3. water-soluble nonpolyol nonocclusives and mixtures thereof.

Some examples of more preferred nonocclusive moisturizers are glycerine, polyethylene glycol, propylene glycol, sorbitol, polyethylene glycol and propylene glycol ethers of methyl glucose (e.g. methyl glucam E-20), polyethylene glycol and propylene glycol ethers of lanolin alcohol (e.g. Solulan-75), sodium pyrrolidone carboxylic acid, lactic acid, urea, L-proline, guanidine, pyrrolidone, hydrolyzed protein and other collagen-derived proteins, aloe vera gel, acetamide MEA and lactamide MEA and mixtures thereof. Of the above, examples of moisturizers are PEG-7 glyceryl cocoate and PEG-10 soya sterol. Another preferred moisturizer is Finsolv TN which is an alkylbenzoate.

The preferred level of such moisturizers is from about 0.05% to about 15% by weight, preferably between 0.5% to about 10% by weight based on the total amount of the ingredients present in the slurry.

Some examples of more preferred nonocclusive moisturizers are polybutene, squalane, sodium pyrrolidone carboxylic acid, D-panthenol, lactic acid, L-proline, guanidine, pyrrolidone, hydrolyzed protein and other collagen-derived proteins, aloe vera gel, acetamide MEA and lactamide MEA and mixtures thereof.

Detergents

Amphoteric detergents may also be incorporated into these hydrophilic polymers. These detergents can be employed in a compatible proportion and manner with the nonionic-anionic surfactants, and may comprise about 0.05-10%, preferably 1-5% of the aqueous phase.

Examples of amphoteric detergents which may be employed include the fatty imidazolines, such as 2-coco-1-hydroxyethyl-1-carboxymethyl-1-hydroxyl-imidazoline and similar products made by reacting monocarboxylic fatty acids having chain lengths of 10-24 carbon atoms with 2-hydroxyethyl ethylene diamine and with monohalo monocarboxylic fatty acids having from 2 to 6 carbon atoms; the fatty beta-alanines such as dodecyl beta-alanine, the inner salt of 2-trimethylamino lauric acid, and betaines such as N-dode-cyl-N,N-dimethylamino acetic acid and the like.

Fragrances

Minor, but effective amount of fragrance selected so as to be chemically-compatible with the above-described surfactants are preferably included in the aqueous phase for cosmetic purposes. Useful fragrances will include, for instance about 0.025-2%, preferably about 0.05-1.5% of floral oils such as rose oil, lilac, jasmine, wisteria, lemon, apple blossom, or compounds bouquets such as spice, aldehydic, woody, oriental, and the like.

Other Optional Ingredients

Minor amounts of other adjuvants, such as dyes, flame retardants and the like, may be introduced into the present products in effective amounts either via the aqueous or resin phase or by treating the final product with the adjuvants as by spraying, mixing, etc. Other optional ingredients include topical dermatological drug ingredients that could be useful such as antihistamines, antibiotics, antifungal agents, sunscreen agents, etc. anti-acne drugs, corticosteroids like betamethasone dipropionate, fluocinide, etc.

Emollient esters, mineral oils, silicone and other solvents can be incorporated into the polymer film for release. These items can be encapsulated or just added as a liquid phase ingredient. Natural ingredients can be used such as avocado oil, vitamins, such as A, C or E, natural plant emollients, or natural cleansing agents etc. Fragrances, anti-bacterial agents and topical drug ingredients (certain types) could be incorporated too.

The samples are coated (100% coverage) on 55 GSM Spunlace Blend non-woven fabric. The active ingredients were coated on the nonwoven using a Meyer rod, which coats the total surface (like a doctor blade). A printing technique for the application of the active ingredients that would give better control the amount of ingredients necessary to do the job and it will improve the appearance.

These samples truly function as a moisturizing cleanser. When the cloth is moistened with water, it works up into a warm, sudsy cleansing lotion that feels great. Preferably, is a light, fresh fragrance is used. This can be changed relatively easily if it is not acceptable to the user.

The invention will be further described by reference to the following detailed examples.

In Example 1, the following ingredients were mixed together, water, Sodium laureth sulfate (50% active), Cocoamidopropyl amine oxide (30% active), PEG-7 glyceryl cocoate, PEG-10 soya sterol, Diatomaceous earth and Hydrophilic polyurethane prepolymer to form a aqueous slurry. The aqueous slurry was coated on a textile material. The formulation is described in Table 1 below:

TABLE 1

New Water Activated Dry Cleansing Cloth

| Ingredients | Formula % | Dried Film Solids | % Solids in Film |
|---|---|---|---|
| Water | 4.00 | 2.50 | 3.57 |
| Sodium laureth sulfate (50% active) | 50.00 | 25.00 | 35.71 |
| Cocoamidopropyl amine oxide (30% active) | 5.00 | 1.50 | 1.05 |
| PEG-7 glyceryl cocoate | 2.00 | 2.00 | 2.86 |
| PEG-10 soya sterol | 2.00 | 2.00 | 2.86 |
| Diatomaceous earth | 7.00 | 7.00 | 10.00 |
| Hydrophilic polyurethane prepolymer | 30.00 | 30.00 | 42.86 |
| | 100.00 | 70.00 | 100.00 |

| | | Components in Coating (2 g.) | |
|---|---|---|---|
| Substrate | 2.5 grams | | |
| Coating | 2.0 grams | Water | 0.0714 |
| Total | 4.5 grams | Surfactants | 0.7352 |
| | | Moisturizers | 0.1144 |
| | | Filler | 0.2000 |
| | | Polymer | 0.8572 |
| | | Total | □2.0 g. |

0.7352/2.5 g. = 29% surfactant based on weight of nonwoven 0.7352/3.36 g = 18.81% surfactant based on weight of nonwoven + polymer The textile sheet performs the dual function of reinforcing the sheet and providing a nonabrasive cleaning and wiping surface on the pad. When moistened, these double-surfaced pads are useful for cleaning a wide variety of porous and nonporous household or workplace surfaces, such as countertops, appliances or bathroom fixtures, including surfaces formed of wood, linoleum, metal, porcelain, glass, plastics or ceramics. At low levels of polymer and high water content of the aqueous phase, a premoistened ready to use skin cleansing system is apparent. In any case, additional water could be added to the final cloths and then used as a ready to use product.

Additional formulations are shown in the following tables:

TABLE 2

Aqueous-Phase Detergent Formulations - Nanofoam Films
Formulations reacted with hydrophilic polyurethane pre-polymers & coated on nonwoven

| | % Ingredients | | | | | | | | | |
|---|---|---|---|---|---|---|---|---|---|---|
| Ingredients | 1 | 2 | 3 | 4 | 5 | 6 | 7 | 8 | 9 | 10 |
| Water | 35.07 | 35.07 | 35.07 | 35.07 | 35.05 | 0 | 35.07 | 35.07 | 35.07 | 35.07 |
| Standapol ES-350 | 41.09 | 0 | 16.44 | 20.54 | 36.98 | 0 | 0 | 0 | 0 | 32.87 |
| Standapol LF | 0 | 41.09 | 24.65 | 20.54 | 4.11 | 0 | 0 | 0 | 0 | 8.22 |
| Standapol ES-3 | 0 | 0 | 0 | 0 | 0 | 76.16 | 0 | 0 | 0 | 0 |
| Sulfatex NL-60 | 0 | 0 | 0 | 0 | 0 | 0 | 41.09 | 0 | 0 | 0 |
| Standapol EA-40 | 0 | 0 | 0 | 0 | 0 | 0 | 0 | 41.09 | 0 | 0 |
| Standapol ES-40 | 0 | 0 | 0 | 0 | 0 | 0 | 0 | 0 | 41.09 | 0 |
| Velvatex BA-35 | 5.48 | 5.48 | 5.48 | 5.48 | 5.48 | 5.48 | 5.48 | 5.48 | 5.48 | 5.48 |
| Cetiol HE | 6.85 | 6.85 | 6.85 | 6.85 | 6.85 | 6.85 | 6.85 | 6.85 | 6.85 | 6.85 |
| Celite SFSF | 10.96 | 10.96 | 10.96 | 10.96 | 10.96 | 10.96 | 10.96 | 10.96 | 10.96 | 10.96 |

TABLE 2-continued

| | | | | | | | | | | |
|---|---|---|---|---|---|---|---|---|---|---|
| TZ-37 | 0.41 | 0.41 | 0.41 | 0.41 | 0.41 | 0.41 | 0.41 | 0.41 | 0.41 | 0.41 |
| Kathon CB | 0.14 | 0.14 | 0.14 | 0.14 | 0.14 | 0.14 | 0.14 | 0.14 | 0.14 | 0.14 |
| | 100 OK | 100 Too thick | 100 OK | 100 Good | 100 Good | 100 Too thick | 100 Gelled | 100 Gelled | 100 Gel | 100 Very good |

Final Formulations Coated on Nonwoven
Aqueous phase 70.00%
Rynel Trepol ® prepolymer 30.00%
Notes:
Coated samples #4 and #10 appeared to be best. Coating was approximately 3 grams per 6 × 7" sheet

TABLE 3

Hydrophilic Polyurethane Nanofoam Film Formulations
Evaluation Of "Betaine" Alternate Materials

| Ingredients | 1 | 2 | 3 | 4 | 5 |
|---|---|---|---|---|---|
| Water | 36.6492 | 36.6492 | 36.6492 | 36.6492 | 31.0140 |
| Steol CS-370 | 20.5380 | 20.5380 | 20.5380 | 20.5380 | 0 |
| Rhodapex PS-603 | 0 | 0 | 0 | 0 | 11.9840 |
| Standapol LF | 0 | 0 | 0 | 0 | 14.3780 |
| Cetilol HE | 0.7000 | 0.7000 | 0.7000 | 0.7000 | 0.7000 |
| Velvatex BA-35 | 0 | 0 | 0 | 0 | 3.8600 |
| Crodsultaine C-50 | 3.8360 | 0 | 0 | 0 | 0 |
| Crodasinic LS-30 | 0 | 3.8360 | 0 | 0 | 0 |
| Macanate LO Special | 0 | 0 | 3.8360 | 0 | 0 |
| Makanate DC-50 | 0 | 0 | 0 | 3.8360 | 0 |
| Celite SFSF | 7.6790 | 7.6790 | 7.6790 | 7.6790 | 7.6790 |
| Fragrance TZ-37 | 0.2870 | 0.2870 | 0.2870 | 0.2870 | 0.2870 |
| Kathon CG | 0.0980 | 0.0980 | 0.0980 | 0.0980 | 0.0980 |
| Methyl Paraben | 0.2030 | 0.2030 | 0.2030 | 0.2030 | 0 |
| Propyl Paraben | 0.0098 | 0.0098 | 0.0098 | 0.0098 | 0 |
| Trepol ® Polymer | 30.0000 | 30.0000 | 30.0000 | 30.0000 | 30.0000 |
| | 100 | 100 | 100 | 100 | 100 |

Formulations were coated on nonwoven substrate - 2 to 3 grams per 6 × 7½" sheet

TABLE 4

Aqueous Phase Detergent Formulations -
Various Moisturizing Components - Nanofoam Films
Formulations reacted with hydrophilic polyurethane pre-polymer & coated on Nonwoven

| Ingredients | 1 | 2 | 3 | 4 | 5 | 6 | 7 | 8 |
|---|---|---|---|---|---|---|---|---|
| Water | 46.486 | 46.486 | 46.486 | 46.486 | 46.486 | 46.486 | 46.486 | 46.486 |
| Steol CS-370 | 14.670 | 14.670 | 14.670 | 14.670 | 14.670 | 14.670 | 14.670 | 14.670 |
| Standapol LF | 20.540 | 20.540 | 20.540 | 20.540 | 20.540 | 20.540 | 20.540 | 20.540 |
| Velvatex BA-35 | 5.480 | 5.480 | 5.480 | 5.480 | 5.480 | 5.480 | 5.480 | 5.480 |
| Incrocas 30 | 1.000 | 0 | 0 | 0 | 0 | 0 | 0 | 0 |
| Procetyl AWS | 0 | 1.000 | 0 | 0 | 0 | 0 | 0 | 0 |
| Glycerox 767 | 0 | 0 | 1.000 | 0 | 0 | 0 | 0 | 0 |
| Dermol 618 | 0 | 0 | 0 | 1.000 | 0 | 0 | 0 | 0 |
| Schercemol DISD | 0 | 0 | 0 | 0 | 1.000 | 0 | 0 | 0 |
| MPDIOL Glycol | 0 | 0 | 0 | 0 | 0 | 1.000 | 0 | 0 |
| Lipocol L-12 | 0 | 0 | 0 | 0 | 0 | 0 | 1.000 | 0 |
| Crodamol PMP | 0 | 0 | 0 | 0 | 0 | 0 | 0 | 1.000 |
| Celite SFSF | 10.970 | 10.970 | 10.970 | 10.970 | 10.970 | 10.970 | 10.970 | 10.970 |
| TZ-37 | 0.410 | 0.410 | 0.410 | 0.410 | 0.410 | 0.410 | 0.410 | 0.410 |
| Kathon CG | 0.140 | 0.140 | 0.140 | 0.140 | 0.140 | 0.140 | 0.140 | 0.140 |
| Methyl paraben | 0.290 | 0.290 | 0.290 | 0.290 | 0.290 | 0.290 | 0.290 | 0.290 |
| Propyl paraben | 0.014 | 0.014 | 0.014 | 0.014 | 0.014 | 0.014 | 0.014 | 0.014 |
| | 100 | 100 | 100 | 100 | 100 | 100 | 100 | 100 |

Final formulations coated on nonwoven
Aqueous phase 70.00%
Rynel Trepol ® prepolymer 30.00%

TABLE 5

Aqueous Phase Detergent/Polymer Formulations -
Combination Polymer/Hydrophilic Polyurethane Prepolymer Systems Combination Polymer Hydrophilic Polyurethan Film Formulations

| Composition | 1A | 2B | 3C | 4D | 5E | 6F | 7G | 8H | 9I |
|---|---|---|---|---|---|---|---|---|---|
| Water | 36.862 | 36.862 | 30.862 | 30.862 | 30.862 | 30.862 | 30.862 | 30.862 | 30.862 |
| Steol CS-370 | 20.538 | 20.538 | 20.538 | 20.538 | 20.538 | 20.538 | 20.538 | 20.538 | 20.538 |
| PVP/VA I-335 | 1.400 | 0 | 0 | 0 | 0 | 0 | 0 | 0 | 0 |
| PVP/VA-I-535 | 0 | 1.400 | 0 | 0 | 0 | 0 | 0 | 0 | 0 |
| PVP/VA I-735 | 0 | 0 | 1.400 | 0 | 0 | 0 | 0 | 0 | 0 |
| PVP/VA W-735 | 0 | 0 | 0 | 1.400 | 0 | 0 | 0 | 0 | 0 |
| Copolymer 845 | 0 | 0 | 0 | 0 | 1.400 | 0 | 0 | 0 | 0 |
| Copolymer 937 | 0 | 0 | 0 | 0 | 0 | 1.400 | 0 | 0 | 0 |
| Stableze QM | 0 | 0 | 0 | 0 | 0 | 0 | 1.400 | 0 | 0 |
| PVP K-25 | 0 | 0 | 0 | 0 | 0 | 0 | 0 | 1.400 | 0 |
| Acusol 43OND | 0 | 0 | 0 | 0 | 0 | 0 | 0 | 0 | 1.400 |
| Velvatex BA-35 | 3.836 | 3.836 | 3.836 | 3.836 | 3.836 | 3.836 | 3.836 | 3.836 | 3.836 |
| Celite SFSF | 6.979 | 6.979 | 6.979 | 6.979 | 6.979 | 6.979 | 6.979 | 6.979 | 6.979 |
| TZ-37 | 0.287 | 0.287 | 0.287 | 0.287 | 0.287 | 0.287 | 0.287 | 0.287 | 0.287 |
| Kathon CG | 0.098 | 0.098 | 0.098 | 0.098 | 0.098 | 0.098 | 0.098 | 0.098 | 0.098 |
| Trepol ® Prepolymer | 30.000 | 30.000 | 30.000 | 30.000 | 30.000 | 30.000 | 30.000 | 30.000 | 30.000 |
| TOTAL | 100 | 100 | 100 | 100 | 100 | 100 | 100 | 100 | 100 |

TABLE 6

Non-polyurethane Formulations -
Water soluble/Dispersable polymers

Combination Polymer Hydrophilic Polyurethan Film Formulations

| Composition | 1A | 2B | 3C | 4D | 5E | 6F | 7G | 8H | 9I |
|---|---|---|---|---|---|---|---|---|---|
| Water | 52.66 | 52.66 | 52.66 | 52.66 | 52.66 | 52.66 | 52.66 | 52.66 | 52.66 |
| Steol CS-370 | 29.34 | 29.34 | 29.34 | 29.34 | 29.34 | 29.34 | 29.34 | 29.34 | 29.34 |
| PVP/VA I-335 | 2.00 | 0 | 0 | 0 | 0 | 0 | 0 | 0 | 0 |
| PVP/VA-I-535 | 0 | 2.00 | 0 | 0 | 0 | 0 | 0 | 0 | 0 |
| PVP/VA I-735 | 0 | 0 | 2.00 | 0 | 0 | 0 | 0 | 0 | 0 |
| PVP/VA W-735 | 0 | 0 | 0 | 2.00 | 0 | 0 | 0 | 0 | 0 |
| Copolymer 845 | 0 | 0 | 0 | 0 | 2.00 | 0 | 0 | 0 | 0 |
| Copolymer 937 | 0 | 0 | 0 | 0 | 0 | 2.00 | 0 | 0 | 0 |
| Stableze QM | 0 | 0 | 0 | 0 | 0 | 0 | 2.00 | 0 | 0 |
| PVP K-25 | 0 | 0 | 0 | 0 | 0 | 0 | 0 | 2.00 | 0 |
| Acusol 43OND | 0 | 0 | 0 | 0 | 0 | 0 | 0 | 0 | 2.00 |
| Velvatex BA-35 | 5.48 | 5.48 | 5.48 | 5.48 | 5.48 | 5.48 | 5.48 | 5.48 | 5.48 |
| Celite SFSF | 9.97 | 9.97 | 9.97 | 9.97 | 9.97 | 9.97 | 9.97 | 9.97 | 9.97 |
| TZ-37 | 0.41 | 0.41 | 0.41 | 0.41 | 0.41 | 0.41 | 0.41 | 0.41 | 0.41 |
| Kathon CG | 0.14 | 0.14 | 0.14 | 0.14 | 0.14 | 0.14 | 0.14 | 0.14 | 0.14 |
| TOTAL | 100 | 100 | 100 | 100 | 100 | 100 | 100 | 100 | 100 |

These systems were coated on non-woven substrates and dried in an oven for 10 minutes at 160° F. The coating was approximately 2 grams per 6"×7.5" sheet.

Examples of facial wipes are disclosed below. In the examples the assumption is 1.33 square feet per sheet=192 square inches (16"×12" sheet). For moisture loss a Cenco set 50% with initial weights taken at 0 time, 5 minutes and 15 minutes. For qualitative flash foam/foam volumes, 0.20 grams of sheet product into 25 grams distilled water at 30 to 35° C. The product was exposed to water for one minute then shaken manually to a 5 second count.

TABLE 7

Facial wipes

| Composition | Gross wt. | Non-woven wt. | Lay-down wt. | Lay-down gm/sq ft | Lay-down 6 × 7.5 sheet | Initial weight | Moisture loss 15 min. wt | % loss |
|---|---|---|---|---|---|---|---|---|
| Sultaine C-50 | 15.01 | 6.12 | 8.89 | 6.68 | 2.08 | 0.9958 | 0.9785 | 1.7 |
| Sarcosinate LS-30 | 14.27 | 6.16 | 8.11 | 6.10 | 1.90 | 0.8550 | 0.8301 | 2.9 |

TABLE 7-continued

Facial wipes

| Composition | Gross wt. | Non-woven wt. | Lay-down wt. | Lay-down gm/sq ft | Lay-down 6 × 7.5 sheet | Initial weight | Moisture loss 15 min. wt | % loss |
|---|---|---|---|---|---|---|---|---|
| Silicone Sarcosinate DC-50 | 15.57 | 5.83 | 9.74 | 7.32 | 2.28 | 1.1086 | 1.0885 | 1.8 |
| PVP/VA I-335 | 13.54 | 6.25 | 7.29 | 5.48 | 1.71 | 0.8961 | 0.8731 | 2.6 |
| PVP/VA-I-535 | 14.13 | 6.27 | 7.86 | 5.91 | 1.84 | 0.8299 | 0.8028 | 3.3 |
| PVP/VA I-735 | 13.32 | 6.48 | 6.84 | 5.14 | 1.60 | 0.9050 | 0.8817 | 2.6 |
| PVP/VA W-735 | 13.98 | 6.42 | 7.56 | 5.68 | 1.77 | 0.8798 | 0.8575 | 2.5 |
| Copolymer 845 | 13.09 | 6.29 | 6.80 | 5.11 | 1.59 | 0.8183 | 0.7973 | 2.6 |
| Copolymer 937 | 13.23 | 6.45 | 6.78 | 5.10 | 1.59 | 0.9191 | 0.8965 | 2.5 |
| Stableze EZ (no prepolymer) | 11.22 | 6.22 | 5.00 | 3.76 | 1.17 | | | |
| PVP K-25 | 13.34 | 6.37 | 6.97 | 5.24 | 1.63 | | | |
| Acusol 46OND | 11.13 | 6.38 | 4.75 | 3.57 | 1.11 | | | |
| Oil of Olay | | | | | | 0.6228 | 0.5960 | 4.3 |
| Noxema | | | | | | 1.0239 | 0.9971 | 2.6 |
| Steol Base | | | | | | 1.0605 | 1.0482 | 1.2 |

One of the embodiments of the invention is again related to a cleansing system including hydrophilic polyurethane-filled systems, nanofoam films or coatings. The polymer base is water insoluble, but will absorb water to release active ingredients.

Another embodiment is the combination of polymer systems plus hydrophilic polymers, such as polyurethane polymer filled systems. The combined polymer base is water insoluble, but will absorb water to release active ingredients. The combined polymers effect performance of film (i.e. enhance sudsiness, moisturizing activity etc.)

A still further embodiment is non-polyurethane polymer filled systems water or non-water soluble films or coatings. The polymer can either be totally water soluble or insoluble, but filled with active ingredients than can release with water. The systems can be water based or solvent based.

All of these systems can be coated on a variety of substrates, such as non-woven, paper, fabric, plastic, foam, etc. Some systems will not require a substrate and can be cast into usable durable films that are water activated.

All the references discussed in this application are incorporated by reference in their entirety for all useful purposes.

While there is shown and described certain specific structures embodying the invention, it will be manifest to those skilled in the art that various modifications and rearrangements of the parts may be made without departing form the spirit and scope of the underlying inventive concept and that the same is not limited to the particular forms herein shown and described.

We claim:

1. A method of making a cleaning article comprising the steps of:
   (a) forming a wet mixture by mixing water, at least one surfactant, a hydrophilic polyurethane polymer and at least one hydrophilic non-polyurethane polymer selected from the group consisting of monoalkyl esters of polymethyl vinyl ether/maleic acid copolymers, quarternized copolymers of vinylpyrrolidone and dimethylaminoethyl methacrylate, vinylpyrrolidone/vinyl acetate copolymers, alkylated vinylpyrrolidone polymers, polyvinyl pyrrolidone, polyethylene glycols, polyacrylate copolymers, polyvinylidene dichloride, and mixtures thereof;
   (b) impregnating and/or coating a substrate with the wet mixture in such manner that the wet mixture does not form a hydrophilic foam,
   (c) drying the impregnated and/or coated substrate.

2. The method of claim 1, wherein the cleaning article is impregnated and/or coated with a composition comprising
   (a) between about 0.01% and about 90% of a combination of a hydrophilic polyurethane polymer and at least one hydrophilic non-polyurethane polymer;
   (b) between about 0.05% and about 90% of at least one surfactant; and
   (c) between about 10% and about 85% water,
where percentages are based on the total weight of the composition.

3. The method of claim 1, wherein the cleaning article is impregnated and/or coated with between about 1% and about 45% of a combination of a hydrophilic polyurethane polymer and at least one hydrophilic non-polyurethane polymer polymer; between about 20% and about 60% of at least one surfactant; between about 20% and about 60% water; and a component selected from the group consisting of organic fillers, inorganic fillers, abrasives, moisturizers, detergents, fragrances, dyes, flame retardants, antihistamines, antibiotics, antifungal agents, sunscreen agents, anti-acne drugs, corticosteroids, and mixtures of these, where percentages are based on the total weight of the wet mixture.

4. The method of claim 1, wherein the total amount of the combination of hydrophilic polyurethane polymer and at least one hydrophilic non-polyurethane polymer is between about 1% and about 45%, where percentages are based on the total weight of the wet mixture.

5. The method of claim 1, wherein the surfactant is an anionic surfactant, a non-ionic surfactant, or a mixture of both.

6. The method of claim 1, wherein the surfactant is present in an amount between about 20% and about 60%, where percentages are based on the total weight of the wet mixture.

7. The method of claim 1, wherein the water is present in an amount between about 20% and about 60%, where percentages are based on the total weight of the wet mixture.

8. The method of claim 1, wherein the wet mixture further comprises a component selected from the group consisting of organic fillers, inorganic fillers, abrasives, moisturizers, detergents, fragrances, dyes, flame retardants, antihistamines, antibiotics, antifungal agents, sunscreen agents, anti-acne drugs, corticosteroids, and mixtures of these.

9. The method of claim 1, wherein the wet mixture comprises between about 25% and about 35% of a combination of a hydrophilic polyurethane polymer and at least one hydrophilic non-polyurethane polymer selected from the group consisting of monoalkyl esters of polymethyl vinyl ether/maleic acid copolymers, quaternized copolymers of vinylpyrrolidone and dimethylaminoethyl methacrylate, vinylpyrrolidone/vinyl acetate copolymers, alkylated vinylpyrrolidone polymers, polyvinyl pyrrolidone, polyethylene glycols, polyacrylate copolymers, polyvinylidene dichloride, and mixtures thereof between about 20% and about 60% of at least one surfactant;

between about 20% and about 60% water; and a component selected from the group consisting of organic fillers, inorganic fillers, abrasives, moisturizers, detergents, fragrances, dyes, flame retardants, antihistamines, antibiotics, antifungal agents, sunscreen agents, anti-acne drugs, corticosteroids, and mixtures of these, where percentages are based on the total weight of the wet mixture.

* * * * *